US007396159B2

(12) United States Patent
Utschig et al.

(10) Patent No.: US 7,396,159 B2
(45) Date of Patent: Jul. 8, 2008

(54) X-RAY DETECTOR PANEL METHODS AND APPARATUS

(75) Inventors: Michael John Utschig, Wauwatosa, WI (US); Jessica Anne Galie, Milwaukee, WI (US); Jason Robert Ertel, Stow, OH (US)

(73) Assignee: General Electric Company, Schenectady, NY (US)

( * ) Notice: Subject to any disclaimer, the term of this patent is extended or adjusted under 35 U.S.C. 154(b) by 58 days.

(21) Appl. No.: 11/448,527

(22) Filed: Jun. 7, 2006

(65) Prior Publication Data

US 2007/0286345 A1 Dec. 13, 2007

(51) Int. Cl.
*G21K 4/00* (2006.01)
*G03B 42/04* (2006.01)

(52) U.S. Cl. ........................ 378/189; 378/190; 378/192

(58) Field of Classification Search ................. 378/189, 378/190, 192
See application file for complete search history.

(56) References Cited

U.S. PATENT DOCUMENTS 6,025,598 A * 2/2000 Tago ..................... 250/370.01
6,340,812 B1 1/2002 Izumi et al. ................ 25/208.1
6,342,700 B1 1/2002 Izumi et al. ............ 250/370.13
6,518,557 B1 2/2003 Izumi et al. ............. 250/208.1
6,559,451 B1 5/2003 Izumi et al. ............ 250/370.08
6,603,106 B2 8/2003 Teranuma et al. ........ 250/208.1
6,638,782 B2 10/2003 Izumi et al. ................... 438/30
6,646,266 B2 11/2003 Izumi .................... 250/370.08
6,649,438 B2 11/2003 Izumi et al. ................... 438/30
6,700,126 B2 * 3/2004 Watanabe ............. 250/370.09
6,781,109 B2 8/2004 Izumi et al. .............. 250/214.1
6,798,030 B1 9/2004 Izumi et al. ................. 257/428
6,905,244 B2 * 6/2005 Kilcher et al. .............. 378/170
6,967,333 B2 * 11/2005 Hata ..................... 250/370.11
7,183,556 B2 * 2/2007 Yagi ...................... 250/370.09
7,189,972 B2 * 3/2007 Ertel et al. ............. 250/370.11
7,195,395 B2 * 3/2007 Quarry et al. ............... 378/170
7,202,481 B2 * 4/2007 Spahn et al. ........... 250/370.09
7,210,847 B2 * 5/2007 Hack .......................... 378/189

* cited by examiner

*Primary Examiner*—Edward J. Glick
*Assistant Examiner*—Thomas R Artman
(74) *Attorney, Agent, or Firm*—Fisher Patent Group, LLC; Thomas M. Fisher

(57) ABSTRACT

Apparatus includes a digital x-ray detector panel, a panel support, and a resilient sheet positioned between the panel and the support, the sheet having an area smaller than an area of the panel.

12 Claims, 3 Drawing Sheets

X-RAY DETECTOR PANEL METHODS AND APPARATUS

BACKGROUND OF THE INVENTION

This invention relates generally to methods and apparatus for digital x-ray imaging systems, and more particularly to methods and apparatus for digital x-ray panels.

The panel of a digital x-ray detector generally consists of a glass substrate, upon which the imaging electronics and x-ray conversion materials are deposited. Being glass, the panel is inherently fragile and difficult to constrain. The panel is typically constrained using high-friction materials on its backside to resist lateral (in-plane) motion, or clamping/screwing the connecting electronics to a rigid support and relying on the flex connections to constrain the panel. In some instances the panel is permanently glued to a panel support or frame made of a metallic or plastic material to enable more general mechanical constraints. A disadvantage of bonding the glass permanently to a support is the inability to rework the panel connections in case of damage or failure. Another disadvantage of bonding the glass directly to a support is the direction transfer of shock from the support to the fragile glass panel. As x-ray devices have moved from being fixed devices to being portable devices, the detector is now expected to survive high levels of shock and vibration on a regular basis.

Therefore described below are methods of constraining a panel that is both re-workable and flexible, increasing the life of the panel to shock abuse and allowing for low-cost repair of any damage.

BRIEF DESCRIPTION OF THE INVENTION

In one aspect, apparatus includes a digital x-ray detector panel, a panel support, and a resilient sheet positioned between the panel and the support, the sheet having an area smaller than an area of the panel.

In another aspect, a digital x-ray imaging system is provided. The system includes an x-ray source, an x-ray detector positioned to receive x-rays emitted from the source, and a computer coupled to the source and the detector. The detector includes a digital x-ray detector panel, a panel support, and a resilient sheet positioned between the panel and the support, the sheet having an area smaller than an area of the panel.

In still another aspect, a method includes cutting a cured bonding material positioned between a digital x-ray detector panel and a panel support with a cutting device, repositioning the panel with respect to the support, and bonding the panel to the support in the repositioned position.

DETAILED DESCRIPTION OF THE INVENTION

There are herein provided methods and apparatus useful for imaging systems such as, for example, but not limited to a digital x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Figure 1:
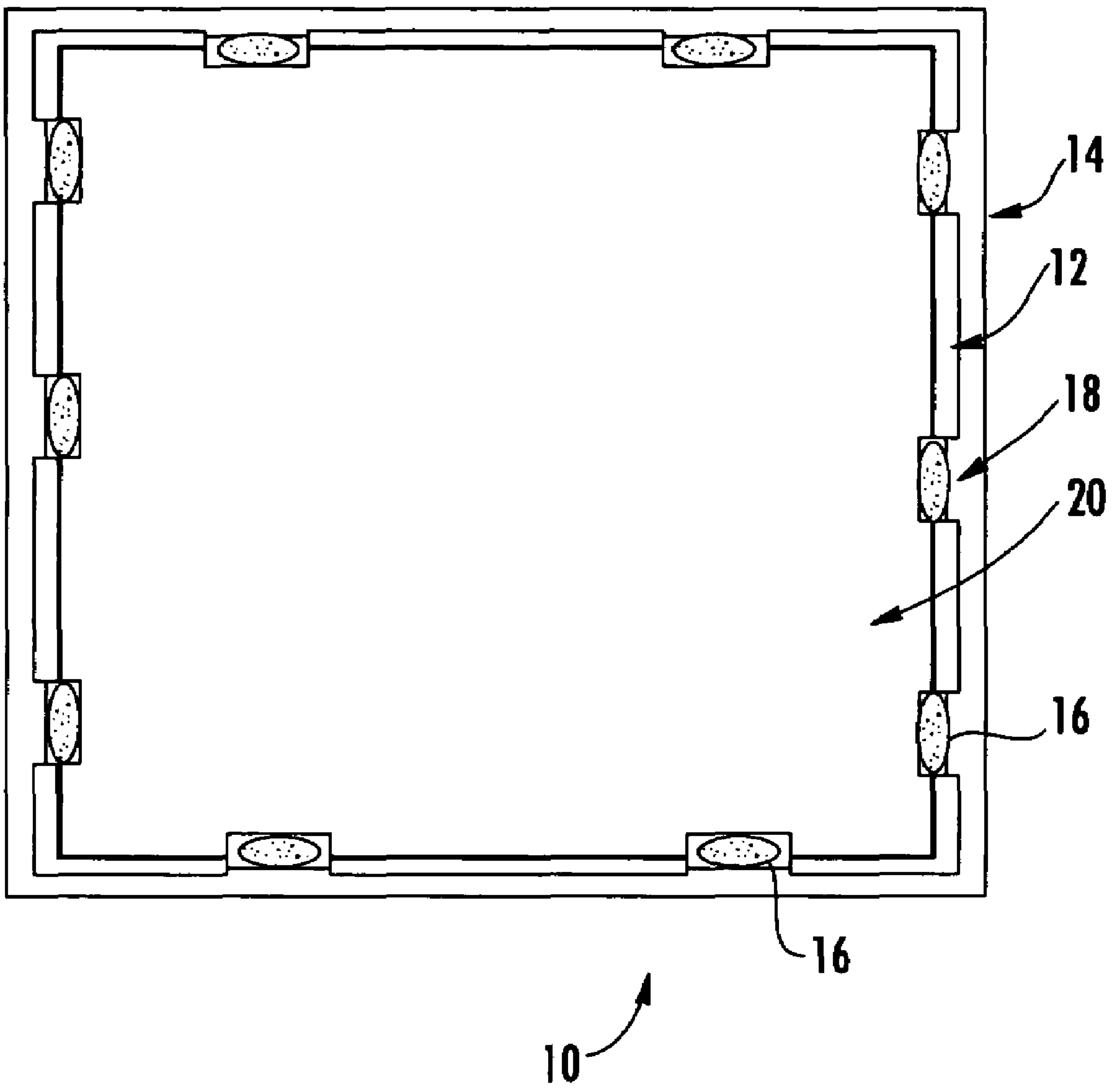
FIG. 1 is a top plan view of a detector assembly.
Figure 2:
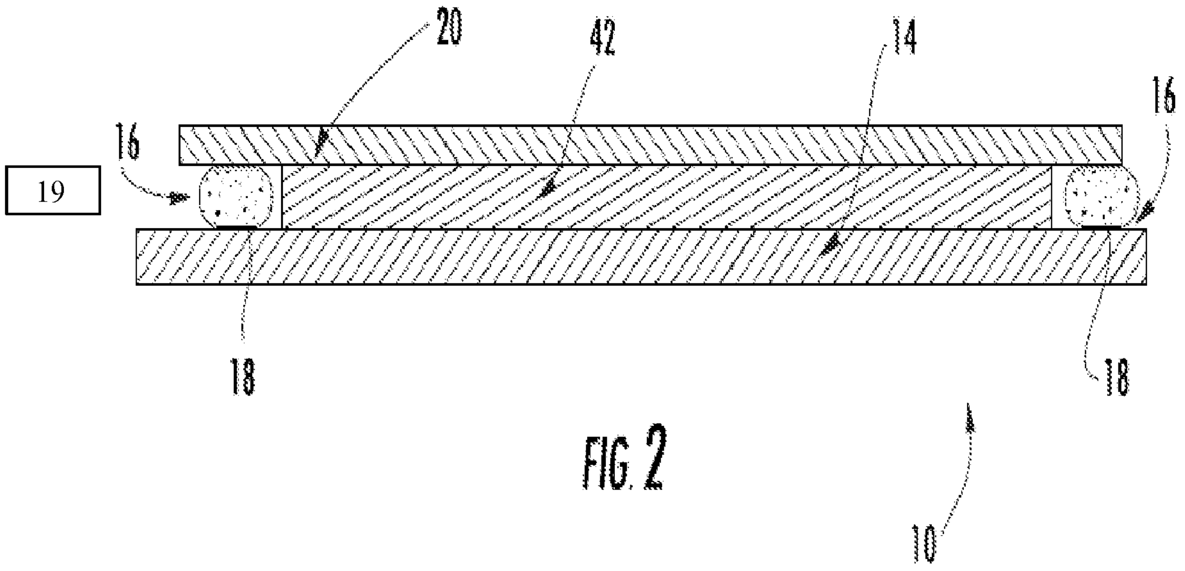
FIG. 2 is a cross-sectional view of the detector assembly illustrated in FIG. 1.

FIG. 1 is a top plan view and FIG. 2 is a cross-sectional view of a portable detector assembly 10. Assembly 10 includes a support foam 12 resting on a panel support 14 with, in accordance with one embodiment, foam cut away in certain regions creating voids 16. The figures further show potting material 18 filling those cutouts within the area of the panel and located, in one embodiment, at the perimeter. An x-ray detector panel 20 is laid over the potting material and bonded at its edges. The cutouts or voids need not be as discrete as shown in the figures, and may be continuous along an edge. The cutouts need not be located along all edges as shown. The voids can be centrally located or could be radially extending slots. FIG. 2 especially illustrates the potting material compressed (while wet and uncured) to the height of the support foam, and curing in that shape.

In one embodiment, the panel support 14 is layered with a thin foam sheet 12 that absorbs out-of plane shocks, distributes point loads, increases lateral friction, and provides a uniform gap between the panel 20 and the support 14 in areas where foam is absent (voids). Additionally, the compliant (resilient) nature of the resilient sheet 12 reduces bending stresses in the panel 20 and the panel support 14 as the assembly 10 is assembled. The support foam is configured to have less surface area than the panel by selectively cutting small areas from it, thereby creating voids for the potting material to fill. Alternatively, the foam sheet can be manufactured with voids. Also, in the embodiment without discrete voids, the sheet can be shaped the same as the support and panel but with smaller dimensions and then the voids are just the places where there is no foam between the panel and the support. Additionally, it is meant herein that the term "area" refers to just the area of the sheet that is over the panel support and under the area of the panel. For example, the total area of the sheet may be greater than the total area of the panel support but positioned such that at least one void is created between the panel support 14 and the panel 20. And thus, the "area" (as used herein) of the sheet in that example is still less than the area of the panel and the panel support. If the small areas are arranged near the perimeter of the foam, they are later accessible from the edge of the stack by an Exacto knife or other thin cutting device 19 for easy removal. The voids are filled with a flexible, wet adhesive such as an RTV (room temperature vulcanizing) silicon manufactured by the General Electric Company. The panel is laid on the support foam, compressing the uncured adhesive to the thickness of the support foam. The stack-up is clamped until the adhesive has cured. The thicknes of the support foam allows the thin knife 19 to cut the RTV and remove the panel from the support. The flexibility of the potting material and the underlying support foam inhibit shock transmission from the panel support. The caulk-like properties of a wet adhesive like an RTV aids positioning during assembly as compared to double-sided tapes.

One advantage is the flexible and re-workable nature of the herein described potting method. The thin, uniform thickness layer of foam and the flexible potting material provide the height necessary to slice the bond. In one embodiment, the resilient sheet (the foam) is about 1/32 in or about 0.8 mm thick. In another embodiment, the sheet's thickness is about 1/16 in or 1.58 mm. The foam provides an inherent cushion.

Typically, the area of sheet compared to the total area of the voids is quite large. For example, in one embodiment the area of the sheet is 90% (or greater) of the area of the panel.

Figure 3:
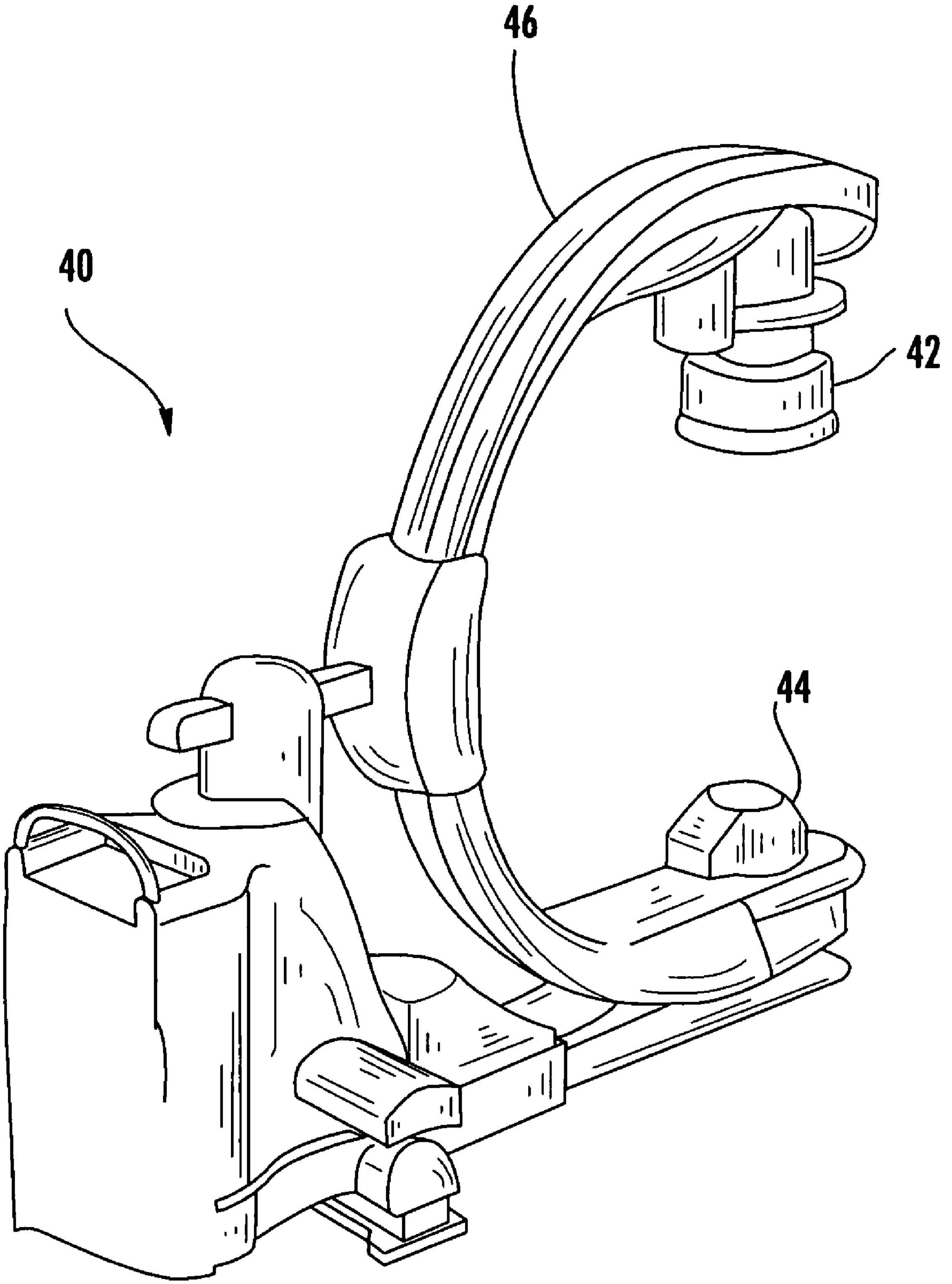
FIG. 3 is a perspective view a digital x-ray imaging system.

FIG. 3 illustrates a digital x-ray imaging system 40 including an x-ray source 42, an x-ray detector 44 positioned to receive x-rays emitted from source 42, and a computer (not shown but in the console of system 40) coupled to the source and the detector. As illustrated in FIGS. 1 and 2, the detector 44 includes a digital x-ray detector panel, a panel support, and a resilient sheet positioned between the panel and the support, wherein the sheet has an area smaller than an area of the panel. Although illustrated as a mobile C-arm 46 imaging system 40, it is contemplated that the benefits of the invention accrue to all digital x-ray systems including stationary systems.

Technical effects of the flexible potting method include the reduction of shock transmissions from the panel support to the panel, the allowance of the panel and/or flexes to be reworked or repaired thus sparing the cost of panel, (flexes are approximately 1/20th the cost of a panel), and the embodiment with the perimeter bond allows other thin sheet-like materials to be inserted between the panel and support in the middle area. Also, the herein described methods and apparatus allow for the re-positioning during assembly compared to double-sided tapes that do not allow for re-positioning. The foam spacer has an additional benefit of thermally isolating the temperature-sensitive panel from the panel support and warm electronics.

It is contemplated that the benefits of the invention accrue to both medical imaging systems and non-medical imaging systems such as those systems typically employed in an industrial setting or a transportation setting, such as, for example, but not limited to, a baggage scanning digital x-ray imaging system for an airport or other transportation center.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. Apparatus comprising:

a digital x-ray detector panel;

a panel support;

a resilient sheet positioned between said panel and said support, said sheet having an area smaller than an area of said panel, and a bonding agent positioned in a cutout void of said resilient sheet.

2. Apparatus in accordance with claim 1 wherein said sheet of substantially uniform thickness.

3. Apparatus in accordance with claim 2 wherein said sheet is in a compressed state.

4. Apparatus in accordance with claim 1 wherein said sheet is in a compressed state.

5. Apparatus in accordance with claim 1 further comprising a bonding agent positioned in a void extending radially of said resilient sheet.

6. Apparatus in accordance with claim 1 further comprising a bonding agent positioned in a plurality of voids in a perimeter of said resilient sheet.

7. A digital x-ray imaging system comprising:

an x-ray source;

an x-ray detector positioned to receive x-rays emitted from said source; and a computer coupled to said source and said detector, said detector comprising:

a digital x-ray detector panel;

a panel support;

a resilient sheet positioned between said panel and said support, said sheet having an area smaller than an area of said panel, and a bonding agent positioned in a void through said resilient sheet.

8. A system in accordance with claim 7 wherein said sheet of substantially uniform thickness.

9. A system in accordance with claim 8 wherein said sheet is in a compressed state.

10. A system in accordance with claim 7 wherein said sheet is in a compressed state.

11. A system in accordance with claim 10 further comprising a bonding agent positioned in a void extending radially in said resilient sheet.

12. A system in accordance with claim 11 further comprising a bonding agent positioned in a plurality of voids in a perimeter of said resilient sheet.

* * * * *